US005214208A

United States Patent [19]

Tanaka et al.

[11] Patent Number: 5,214,208

[45] Date of Patent: May 25, 1993

[54] TONER CONTAINING A DIMER OF DIARYLGUANIDINE TYPE COMPOUND FOR DEVELOPING ELECTROSTATIC IMAGE

[75] Inventors: Katsuhiko Tanaka; Kazuyoshi Hagiwara, both of Yokohama, Japan

[73] Assignee: Canon Kabushiki Kaisha, Tokyo, Japan

[21] Appl. No.: 764,781

[22] Filed: Sep. 24, 1991

Related U.S. Application Data

[62] Division of Ser. No. 492,137, Mar. 13, 1990, Pat. No. 5,084,369.

[30] Foreign Application Priority Data

Mar. 13, 1989 [JP] Japan ................................. 1-060497

[51] Int. Cl.[5] ...................... C07C 279/18; G03G 9/08

[52] U.S. Cl. .................................... 564/236; 430/106; 430/106.6; 430/110

[58] Field of Search ................ 564/236; 430/110, 106, 430/106.6

[56] References Cited

U.S. PATENT DOCUMENTS

| | | | |
|---|---|---|---|
| 2,297,691 | 10/1942 | Carlson | 95/5 |
| 3,607,261 | 9/1971 | Amidon | 96/1.8 |
| 3,666,363 | 5/1972 | Tanaka et al. | 355/17 |
| 4,663,263 | 5/1987 | Ikeda et al. | 430/110 |
| 4,981,965 | 1/1991 | Yabuki et al. | 564/236 |

FOREIGN PATENT DOCUMENTS 0179642 4/1986 European Pat. Off. .

OTHER PUBLICATIONS

Patent Abstracts of Japan, vol. 9, No. 62 (P-342) [1785], Mar. 19, 1985 (JP-A-59 195 661 (Canon K.K.) Nov. 6, 1984).

Patent Abstracts of Japan, vol. 12, No. 203 (P-715) [3050], Jun. 11, 1988 (JP-A-635357 (Canon Inc.) Jan. 11, 1988).

Patent Abstracts of Japan, vol. 13, No. 9 (P-811) [3357], Jan. 11, 1989 (JP-A-63 216062 (Nippon Kayaku Co., Ltd.) Sep. 8, 1988).

*Primary Examiner*—Richard L. Raymond
*Assistant Examiner*—Peter G. O'Sullivan
*Attorney, Agent, or Firm*—Fitzpatrick, Cella, Harper & Scinto

[57] ABSTRACT

A toner for developing an electrostatic image comprises a binder resin and a dimer of a diarylguanidine type compound. The dimer is represented by the general formula (I) below:

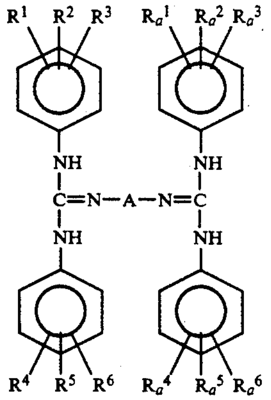

(I)

wherein $R^1$, $R^2$, $R^3$, $R^4$, $R^5$, $R^6$, $R^1a$, $R^2a$, $R^3a$, $R^4a$, $R^5a$, and $R^6a$ are respectively a hydrogen atom, an alkyl group, an amino group, an alkoxy group, or an aryl group which may have a substituent, and may be the same or different from each other; adjacent groups may be linked together to form a ring; and A is a linking group.

2 Claims, No Drawings

TONER CONTAINING A DIMER OF DIARYLGUANIDINE TYPE COMPOUND FOR DEVELOPING ELECTROSTATIC IMAGE

This application is a division of application Ser. No. 07/492,137 filed Mar. 13, 1990, now U.S. Pat. No. 5,084,369.

BACKGROUND OF THE INVENTION

1. Field of the Invention

The present invention relates to a novel toner containing a dimer of a diarylguanidine type compound for developing an electrostatic image in image formation in electronic photography, electrostatic recording, electrostatic printing, and the like.

The present invention relates also to a novel diarylguanidine type compound.

Various methods of electronic photography have been disclosed in U.S. Pat. No. 2,297,691, and Japanese Patent Publication No. 42-23910 (corresponding to U.S. Pat. No. 3,666,363), and Japanese Patent Publication No. 43-24748.

Image developing methods for electronic photography are classified roughly into dry developing methods and wet developing methods. The former is subdivided into methods employing a two-component developing agent and methods employing a one-component developing agent.

As toners for dry developing methods, used, fine powdery materials have been used comprising a dye and/or a pigment dispersed in a natural or synthetic resin. For example, as a one-component developing agent, a powdery toner of finely pulverized binder resin, such as polystyrene, in a size of approximately from 1 to 30 μm in which a coloring agent is dispersed are used. For the magnetic toners, powdery magnetic materials such as magnetite are used. In the case of two-component developing agents, the toner is usually used in combination with a particulate carrier such as glass beads, powdery iron, powdery ferrite or the like.

The toner needs to be charged positively or negatively corresponding to the polarity of the electrostastic latent image to be developed.

For the purpose of giving an electric charge to a toner, triboelectric chargeability of the resin component of the toner may be utilized. In this method, however, the developed image is liable to be fogged because of low chargeability of the toner, giving unsharpened images. In order to impart the desired triboelectric chargeability to the toner, a substance for donating electric chargeability, called a charge-controlling agent, is added thereto.

Charge-controlling agents known in the art include compounds such as nigrosine dyes, azine type dyes, copper phthalocyanine pigments, quaternary ammonium salts, and polymers having a quaternary ammonium salt in a side chain for positive triboelectric charging.

Since some of these charge-controlling agents are liable to contaminate sleeves and carriers, the toner employing such an agent causes deterioration of its triboelectric chargeability and decrease of the image density with repetitive copying. Some kinds of the charge-controlling agents have insufficient triboelectric chargeability and are liable to be affected by temperature and/or humidity, causing fluctuation of the image density depending on change in the surrounding conditions. Some kinds of charge-controlling agents are poorly dispersible in the resin, so that the toner employing such an agent is liable to cause non-uniformity of triboelectric charge quantity between the toner particles, causing fogging. Some kinds of charge-controlling agents are poor in storage stability and may sometimes deteriorate the triboelectric chargeability during a long term storage. Further, some kinds of charge-controlling agents have color, so that they can hardly be used for color toners.

U.S. Pat. No. 4,663,263 describes a toner containing a guanidine derivative. The guanidine derivatives specifically mentioned in this U.S. patent are monomers, which are good positive charge-controlling agents but still have a room for improvement. Some known guanidine derivatives, for example, are found to contaminate toner supporters (e.g., a carrier and a sleeve) when the toner is pulverized to a size of about ⅔ or smaller of usual toner size (e.g., 13 μm), causing gradual lowering of image density. Furthermore, conventional guanidine derivatives can hardly be used with binder resins of high acid value depending on conditions because of the reactivity of the derivatives with acids.

SUMMARY OF THE INVENTION

One object of the present invention is to provide a toner, free from the above-mentioned problems, for developing an electrostatic image.

Another object of the present invention is to provide a toner for developing electrostatic images superior in triboelectric charging characteristics.

Still another object of the present invention is to provide a toner for developing an electrostatic image, which causes little contamination of sleeve or carrier.

A further object of the present invention is to provide a toner for developing an electrostatic image, which has superior environmental stability.

A still further object of the present invention is to provide a toner for developing an electrostatic image, which little deteriorates performance with repetition of copying.

According to one aspect of the present invention, there is provided a toner for developing an electrostatic image, comprising a binder resin and a dimer of a diarylguanidine type compound.

According to another aspect of the present invention, there is provided a novel dimer of diarylguanidine type compound respresented by the formula (II) below:

(II)

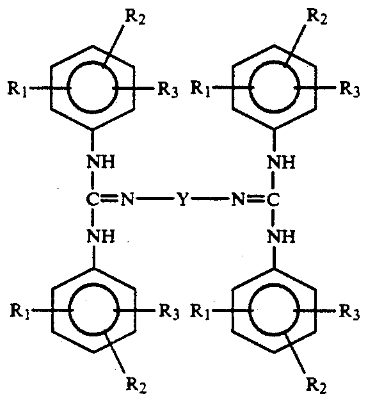

where $R^1$, $R^2$, and $R^3$ are respectively hydrogen, an alkyl group of 1 to 4 carbons, or a phenyl group, which may be the same with or different from each other, and two adjacent groups may be linked together to form a ring, and Y is

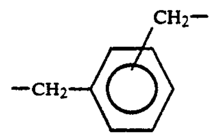

or $-CH=CH-CH_2-$.

DETAILED DESCRIPTION OF THE PREFERRED EMBODIMENT

The present invention relates to a toner, for developing electrostic images, containing a dimer of a diarylguanidine type compound prepared by dimerizing a diarylguanidine derivative with the aid of a linking group. The present invention relates also to a novel dimer of diarylguanidine type compound represented by the Formula (II) below:

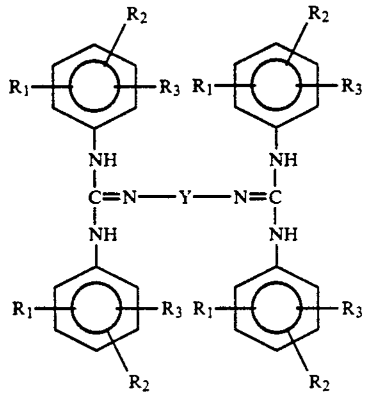

(II)

where $R^1$, $R^2$, and $R^3$ are respectively hydrogen, an alkyl group of 1 to 4 carbons, or a phenyl group, which may be the same with or different from each other, and two adjacent groups may be linked together to form a ring, and Y is

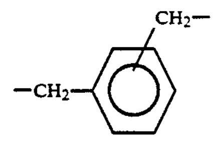

and $-CH=CH-CH_2-$.

The use of the dimer of a diarylguanidine type compound dimerized with the aid of a linking group is novel for a toner for developing electrostatic images.

In particular, the dimers per se represented by the general formula (II) are novel compounds.

The inventors of the present invention, as the results of investigation of guanidine derivatives, have found that a dimer prepared by dimerizing a diarylguanidine type compound compound with the aid of a linking group has larger positive triboelectric chargeability and higher heat stability in comparison with the corresponding undimerized diarylguanidine compound. Further the inventors have found that the diarylguanidine type compounds neither become colored by dimerization by use of the linking group nor involve a problems of chemical safety.

The monomeric guanidine derivatives per se are described in U.S. Pat. No. 4,663,263, and have an excellent positive-charge-controlling property. The inventors of the present invention found the guanidine derivative dimerizable at the nitrogen atom having a double bond through a linking agent. Consequently, the inventors have found that diarylguanidine derivatives come to have more excellent properties particularly by dimerization.

In the present invention, the dimer of the diarylguanidine type compound is preferably represented by the general formula (I):

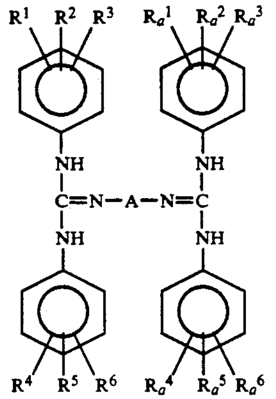

(I)

where $R^1$, $R^2$, $R^3$, $R^4$, $R^5$, $R^6$, $R^1a$, $R^2a$, $R^3a$, $R^4a$, $R^5a$, and $R^6a$ are respectively a hydrogen atom, an alkyl group, an amino group, an alkoxy group, or an aryl group which may have a substituent, and may be the same or different from each other; adjacent groups may be linked together to form a ring; and A is a linking group.

More preferable are the dimers represented by the general formula (Ia) below:

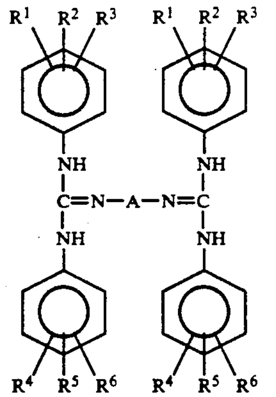

(Ia)

where $R^1$ to $R^6$ mean the same as above.

The linking group A is not specially limited provided that it links the diarylguanidine derivatives stably. The examples of the linking group A are a double-bond-containing linking group such as vinylene group, and $-(CH_2)_{n+1}-$, and 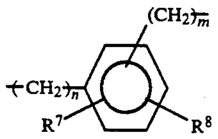

The vinylene-group-containing linking agent A is exemplified by $-(CH{=}CH)_{l+1}-(CH_2)_{n+1}-$.

l, m, and n in the linking groups A are respectively an integer of from 0 to 8, and $R^7$ and $R^8$ are respectively any one of a hydrogen atom, an alkyl group, an amino group, an aryl group, or an alkoxy group, which may be the same or different from each other.

As $R^1$ to $R^6$, and $R^1a$ to $R^6a$ in the formulas, alkyl groups having 1 to 20 carbons are preferable such as methyl, ethyl, n-propyl, isopropyl, t-butyl, and stearyl. Alkoxy groups having 1 to 8 carbons are preferable, which including methoxy, ethoxy, n-propoxy, n-butoxy, t-butoxy, and n-pentoxy. Aryl groups having 6 to 16 carbons or substituted aryl groups are preferable, which including phenyl, substituted phenyl, tolyl, xylyl, and naphthyl. The substituents on the aryl group include alkyl and alkoxy. In the case where any pair of R1 to R6 are adjacent, the adjacent groups may form a ring together. For example, the aryl group having substituents $R^1$ to $R^6$ may be a tetralyl group. The alkyl group, the aryl group, and the alkoxy group denoted by $R^7$ and $R^8$ may be described in the same manner as described above regarding the $R^1$ to $R^6$ groups. It is important in the present invention that the dimer of the diarylguanidine type compound is derived by dimerizing a diarylguanidine derivative with a linking group. This gives capability of retaining a sufficient charge quantity to the toner. The positive triboelectric charge quantity of the dimerized product will vary slightly depending on the substituent of the aryl group of the diarylguanidine. Thereby, the positive triboelectric charge quantity to be given to the toner can be finely adjusted. Generally, an electron-donating substituent increases the chargeability of the dimer, while an electron-attracting substituent decreases the chargeability of the dimer. The aryl group has usually three or less substitutents which may be attached to any of ortho-, meta-, and para-positions, but optionally may have more substituents.

The preferable specific examples of the compounds represented by the Formula (I) are shown below. These are representative examples in consideration of ease of the synthesis thereof. The compounds of the present invention are not limited to these compounds.

Dimer (I-1)

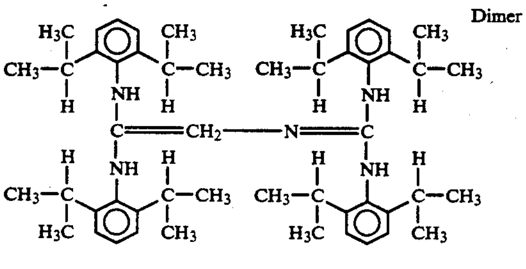

-continued

Dimer (I-2)

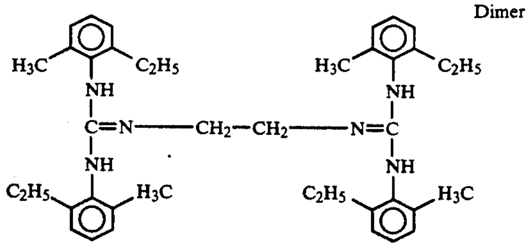

Dimer (I-3)

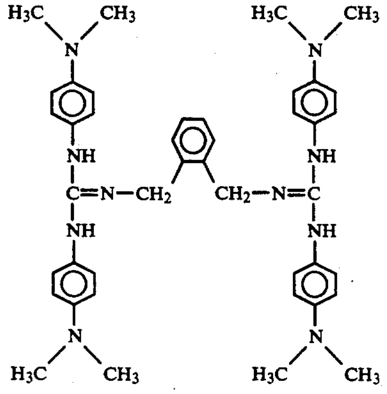

An asymmetric compound derived from dimerizing different diarylguanidine derivatives with a linking group also has excellent positive triboelectric chargeability. When the asymmetric compound is used, it may be used as a mixture of three compounds including two symmetric compounds.

The compound derived by dimerizing a diarylguanidine derivative through a linking group has excellent properties in comparison with the monomeric guanidine derivative.

One of them is an increased positive triboelectric chargeability. While known guanidine derivatives exhibit sufficient positive triboelectric chargeability, the dimer of the present invention exhibits still larger positive triboelectric chargeability. Accordingly, in the present invention, the dimer can achieve the same level of effect with a smaller amount of addition in comparison with the corresponding guanidine derivatives.

Some conventional guanidine derivatives contaminate toner supporters (e.g., a carrier, a sleeve and the like) when the toner is pulverized to a size of ¾ or less of usual toner size, and gradually cause image density to lower. Even with such a guanidine derivatives, the contamination of the toner supporter can be reduced to the level at which no problem arises in the practical use, by changing the derivative to a dimer form as in the present invention.

Some conventional guanidine derivatives can hardly be used in combination with a binder resin of a high acid value because of reactivity of the derivatives with acids. In the present invention, the dimerization reduces the reactivity with acids, whereby the derivative is made readily usable with a binder of a higher acid value in comparison with the conventional guanidine derivatives.

Among the diarylguanidine type compounds represented by the Formula (I), those exhibiting still preferable properties are represented by the Formula (II).

The dimer represented by the Formula (II) specifically include the dimers of from (II-1) to (II-10) below.

(II-I)

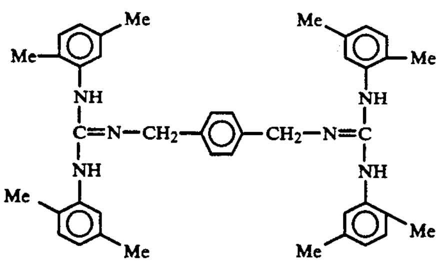

where Me denotes a methyl group, and Et denotes an ethyl group.

(II-2)

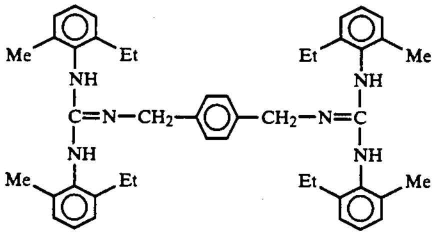

(II-3)

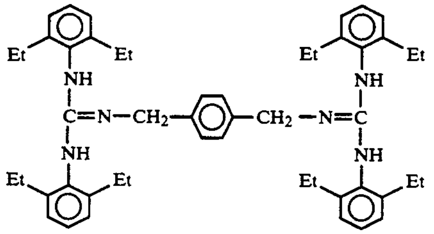

(II-4)

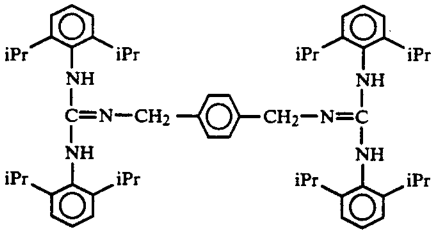

where iPr denotes an isopropyl group.

(II-5)

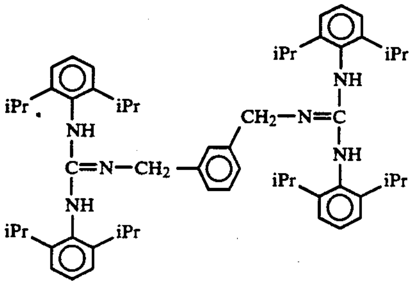

-continued (II-6)

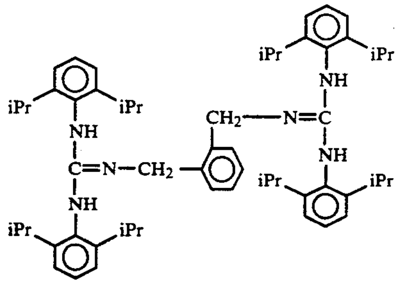

(II-7)

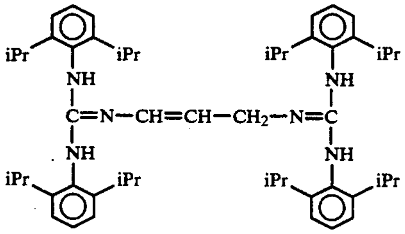

(II-8)

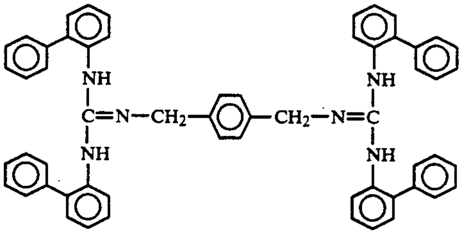

(II-9)

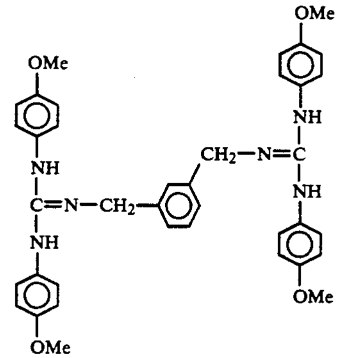

(II-10)

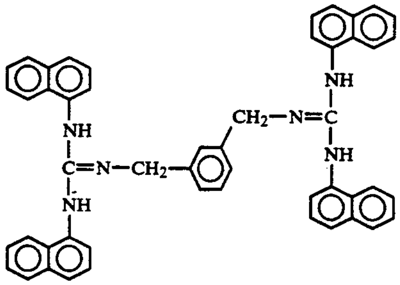

In the present invention, the dimers of diarylguanidine type compounds are not limited to these compounds.

The method of synthesis of the dimer by dimerizing the guanidine derivatives with the aid of a linking group is described in detail in the Examples shown later.

In principle, the dimer is formed by reacting a diarylguanidine derivative with a halogen compound such as $X-(CH_2)_{n+1}-X$, $X-(CH=CH)_{l+1}-(CH_2)_{n+1}-X$ and

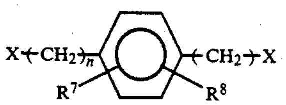

where X denotes a halogen atom. The halogen compounds includes 1,2-bromoethane, xylylene dibromide, and the like.

The dimer of the diarylguanidine type compound can be prepared in such a manner that a known diarylguanidine derivative represented by the Formula (III) below:

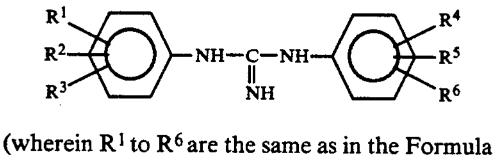
(III)

(wherein $R^1$ to $R^6$ are the same as in the Formula (I).) as a starting material, and ½ equivalent or more, relative to the above derivative, of a halogen compound:

$X-(CH_2)_n-X$, or 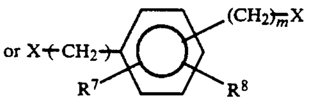

(where X is a halogen atom, and n, m, $R^7$, and $R^8$ are the same as in the Formula (I).) are dissolved in an organic solvent such as chloroform and dimethylformamide, and reacted in the presence of a basic compound as the catalyst, at a reflux temperature of the solvent for 10 hours, and after the catalyst is removed, the reaction mixture is washed, the solvent is distilled off, and the resulting pale brown crystal is recrystallized from an organic solvent such as acetone and chloroform.

The halogen of the halogen compounds includes F, Cl, Br and I.

The resulting dimer can be identified by analysis such as NMR and IR.

The novel dimer represented by the Formula (II) of the present invention is synthesized, for example, by an addition reaction of one equivalent of xylylene diamine and two equivalents of diarylcarboimide; by a dehydrosulfurization condensation reaction of one equivalent of xylylenediamine and two equivalents of diarylthiourea; by dehydrochlorination condensation reaction of one equivalent of $\alpha,\alpha'$-dihalogenoxylene and two equivalents of diarylguanidine (See U.S. Pat. No. 4,663,263 as to the synthesis method): or a dehydration condensation reaction of one equivalent of acrolein and two equivalents of diarylguanidine.

In the toner for developing electrostatic image of the present invention, the addition of the dimer (serving as a charge-controlling agent) gives to the toner a proper positive triboelectric charge quantity without significant influence to the other toner raw materials.

Incorporation of the dimer of a guanidine derivative may be practiced in two methods: namely addition into the interior of a toner particle (internal addition), and blending with toner particles (external addition). The quantity of addition of such a compound cannot be limited definitely since it is decided depending on the kind of the binder resin, presence of an optionally added additive, and a process of manufacturing the toner including the dispersion method. In the case of the internal addition, the dimer is used preferably in an amount of from 0.1 to 10 parts by weight, more preferably from 0.1 to 5 parts by weight per 100 parts by weight of the binder resin. In the case of the external addition, the dimer is used in an amount of 0.01 to 10 parts by weight per 100 parts of the binder resin, and is preferably adhered to the toner surface mechanochemically.

The dimer of the present invention may be used in combination with a known charge-controlling agent.

A toner is basically composed of a coloring material, a binder resin, and other additives. The other constituting components of the toner of the present invention are described below.

The coloring material for the toner of the present invention includes carbon black, lampblack, iron black, ultramarine, nigrosine dyes, aniline blue, phthalocyanine blue, phthalocyanine green, hansa yellow G, rhodamine 66, lake, Chalcooil Blue, chrome yellow, quinacridone, benzidine yellow, Rose Bengal, triarylmethane dyes, monoazo dyes and pigments, and disazo dyes and pigments. These known dyes and pigments may be used, alone or in combination. The non-magnetic dyes or pigments may be used in an amount of from 0.1 to 20 parts by weight, preferably from 0.5 to 10 parts by weight per 100 parts by weight of the binder resin.

The resin includes homopolymers of styrene and substituted styrenes such as polystyrene, poly-p-chlorostyrene, polyvinyltoluene and the like; styrene type copolymers such as styrene-p-chlorostyrene copolymers, styrene-vinyltoluene copolymers, styrene-vinylnaphthalene copolymers, styrene-acrylic ester copolymers, styrene-methacrylic ester copolymers, styrene-methyl $\alpha$-chloromethacrylate copolymers, styrene-acrylonitrile copolymers, styrene-vinylmethylether copolymers, styrene-vinylethylether copolymers, styrene-vinyl methyl ketone copolymers, styrene-butadiene copolymers, styrene-isoprene copolymers, styrene-acrylonitrile-indene copolymers, and the like; polyvinyl chloride resins, phenol resins, modified phenol resins, modified maleic resins, acrylic resins, methacrylic resins, polyvinyl acetate resins, silicone resins, polyester resins, polyurethanes, polyamide resins, furan resins, epoxy resins, xylene resins, polyvinylbutyral resins, terpene resins, coumalon-indene resins, petroleum resins and the like. Among the binder resins, preferable are styrene type copolymers and polyester resins from the standpoint of developing characteristics and fixing properties of the toner.

Crosslinked styrene type copolymers are also preferable for the binder resin. The comonomers to be polymerized with styrene for the styrene type copolymers include substituted and unsubstituted monocarboxylic acids having a double bond such as acrylic acid, methyl acrylate, ethyl acrylate, butyl acrylate, dodecyl acrylate, octyl acrylate, 2-ethylhexyl acrylate, phenyl acrylate, methacrylic acid, methyl methacrylate, ethyl methacrylate, butyl methacrylate, octyl methacrylate, acrylonitrile, methacrylonitrile, acrylamide and the like; substituted and unsubstituted dicarboxylic acids containing a double bond such as maleic acid, butyl maleate, methyl maleate, and dimethyl maleate; vinyl chloride; vinyl esters such as vinyl acetate, vinyl benzoate, and the like; ethylene type olefins such as ethylene, propylene, butylene, and the like; vinyl ketones such as vinyl methyl ketone, vinyl hexyl ketone, and the like; vinyl ethers such as vinyl methyl ether, vinyl ethyl ether, vinyl isobutyl ether, and the like; and other vinyl monomers, which may be used, alone or in combination.

As the crosslinking agent are used compounds having two or more polymerizable double bonds. The examples thereof include aromatic divinyl compounds such as divinylbenzene, and divinylnaphthalene; carboxylic esters having two double bonds such as ethylene glycol diacrylate, ethylene glycol dimethacrylate, 1,3-butanediol dimethacrylate, and the like; divinyl compounds such as divinylaniline, divinyl ether, divinyl sulfide, divinyl sulfone, and the like; and compounds having three or more vinyl groups, which may be used, alone or in combination.

When a pressure-fixing process is employed, a binder resin for pressure-fixing toner may be used. The examples of such resins are polyethylenes, polypropylenes, polymethylenes, polyurethane elastomers, ethylene-ethyl acrylate copolymers, ethylene-vinyl acetate copolymers, ionomer resins, styrene-butadiene copolymers, styrene-isoprene copolymers, linear saturated polyesters, and paraffin wax.

The toner of the present invention may be used as a magnetic toner by incorporating a magnetic material therein. The magnetic material which may be incorporated in the magnetic toner of the present invention includes iron oxides such as magnetite, γ-iron oxide, ferrite, excess iron component type ferrite, and the like; metals such as iron, cobalt, and nickel; alloys of these metals with aluminum, cobalt, copper, lead, magnesium, tin, zinc, antimony, beryllium, bismuth, cadmium, calcium, manganese, selenium, titanium, tungsten, vanadium, and the like; and mixtures thereof.

Such ferromagnetic materials preferably have an average particle diameter within a range of from about 0.1 to about 1 μm, more preferably from 0.1 to 0.5 μm. The amount thereof in the magnetic toner is 40 to 150 parts by weight, preferably 60 to 120 parts by weight, based on 100 parts by weight of the resin component.

As a two-component developing agent, the toner of the present invention is used in a mixture with a powdery carrier. Known carriers may be used in the present invention. The examples thereof include magnetic powders such as iron powder, ferrite powder, nickel powder, and the like and the magnetic powders coated with a resin; and glass beads and those surface-treated with a resin or the like. The resin used therefor includes styrene-acrylic ester copolymers, styrene-methacrylic ester copolymers, acrylic ester copolymers, methacrylic ester copolymers, fluorine-containing resins, silicone resins, polyamide resins, and ionomer resins, and mixtures thereof.

The toner of the present invention may be mixed with an additive, if necessary. The additive includes lubricants such as zinc stearate and the like; abrasive materials such as cerium oxide, silicon carbide and the like; fluidity-donating materials or caking-preventing materials such as fine powdery silica, aluminum oxide and the like; and electroconductivity-donating agents such as carbon black, tin oxide and the like.

The fine powders of fluorine-containing polymers such as polyvinylidene fluoride are preferable additives in view of fluidity, abrasion property, and electric charge stability.

In a preferable embodiment, a wax-like material such as low-molecular-weight polyethylene, low-molecular-weight polypropylene, microcrystalline wax, carnauba wax, sasole wax, paraffin wax, and the like, are added to the toner in an amount of from 0.5 to 5% by weight for the purpose of improving releasability in hot-roll fixing.

The dimers of diarylguanidine derivatives of the present invention, which are substantially colorless, white, or pale-colored, are suitable for a positive chargeability-controlling agent for a color toner such as a cyan toner, a magenta toner, and a yellow toner.

In a preferable method for producing the toner of the present invention, the above-mentioned toner-constituting materials are sufficiently mixed with a mixer such as a ball mill, then the mixture is blended sufficiently using a hot-blender such as a hot-roll kneader and an extruder, the blended matter is cooled to solidify, the cooled matter is mechanically pulverized, and the pulverized matter is classified, thus giving a toner. Other applicable methods include a method in which the constituting materials are dispersed in a binder resin solution, and the dispersion is subjected to spray drying to give a toner; a method in which the materials are mixed with a monomer of a binder resin to give a suspension, and then polymerization is conducted to give a toner; and a method for microcapsule toner comprising a core material and a shell material in which method the materials are incorporated into the core material or the shell material, or the both of them. If necessary, a desired additive is sufficiently mixed with the toner by means of a mixer such as a Henschel mixer to produce a toner of the present invention.

The toner of the present invention can be used for developing an electrostatic image to a visible image in known image-forming methods such as electrophotography, electrostatic recording, and electrostatic printing.

As described above the dimer prepared by dimerization of a guanidine derivative with a linking group is colorless or pale colored, and has great positive triboelectric chargeability. Additionally, it is less hygroscopic. In particular, the dimers of the diarylguanidine type compounds represented by the general Formula (II) have excellent properties.

For this reason, the use of the dimer derived from the guanidine derivative and a linking group as the charge-controlling agent enables the production of a toner for developing an electrostatic image improved in the properties dependent on temperature and humidity. This charge-controlling agent exhibits performances equal to or superior to those of a conventional charge-controlling agent with a smaller quantity of addition, and is less liable to cause problems such as toner supporter contamination which arises by use of conventional charge-controlling agents.

Accordingly, the toner of the present invention causes less variation of image quality depending on variation of environment, and is less liable to cause deterioration of the image quality on continuous copying, and therefore is greatly useful in practical use.

The present invention is specifically explained by referring to Examples. In the description below, the "parts" are based on weight.

EXAMPLE 1

Synthesis of Dimer (II-1)

Into 50 ml of chlorobenzene, 8.5 g (0.03 mole) of N,N'-di(2,5-dimethylphenyl)thiourea, and 2.0 g (0.015 mole) of p-xylylenediamine are added. The mixture was heated to 100° C. Into the solution, 9.3 g (0.012 mole) of basic lead carbonate is added portionwise. After completion of the addition, it was heated and refluxed for 3 hours. The reaction mixture was hot-filtered at 120° C. to eliminate insoluble matters, and cooled by standing. The deposited crystal was collected by filtration to obtain a pale brown crystalline matter. This crystalline matter was recrystallized from chloroform to give 1.6 g of white powder.

Melting point: 193°-196° C.

H-NMR (solvent $CDCl_3$) δ: 2.2 (24H, $CH_3$), 3.65 (4H, broad S, NH), 4.95(4H, S, N—$CH_2$) 6.5-7.4 (16H, m, Arom-H).

IR$\upsilon_{max}$nujol $cm^{-1}$: 3492, 3388(N—H); 1634(C=N).

EXAMPLE 2

Synthesis of Dimer (II-2)

5.9 g (0.02 mole) of N,N'-di(2-methyl-6-ethylphenyl)-guanidine, 2.6 g (0.01 mole) of α,α'-dibromo-p-xylene, and 1.1 g (0.01 mole) of anhydrous sodium carbonate, were added to 50 ml of chloroform, and the mixture was heated and refluxed for 2 hours. Having been cooled by standing, the mixture was washed with water, and concentrated to obtain brown crystalline matter. The brown crystalline matter was separated by chromatography (silica gel: 300 mesh) to give 1.7 g of grayish white powder.

Melting point: 214°-218° C.

H-NMR (solvent: $CDCl_3$) δ: 0.9-1.4 (12H, m, —$CH_3$), 1.9-2.3 (12H, m, ϕ—$CH_3$), 2.2-2.8 (8H, m, ϕ—$CH_2$) 3.4 (4H, S, H—H) 4.6-5.2 (4H, m, N—$CH_2$) 6.8-7.3 (16H, m, Arom-H).

IR$\upsilon_{max}$nujol $cm^{-1}$: 3490, 3380(N—H); 1620(C=N).

EXAMPLE 3

Synthesis of Dimer (II-3)

6.5 g (0.02 mole) of N,N'-di(2,6-diethylphenyl)guanidine 1.8 g (0.01 mole) of α,α'-dichloro-p-xylene, and 1.38 g (0.01 mole) of anhydrous potassium carbonate were added to 50 ml of dimethylforamide. The mixture was heated and refluxed for 5 hours. Thereafter, the solvent was distilled off under a reduced pressure. The residual matter was dispersed in water and was filtered to obtain brown powder, which was recrystallized from benzene, to give 1.2 g of white powder.

Melting point: 209°-213° C.

H-NMR (solvent: $CDCl_3$) δ: 0.9-1.4 (24H, m, —$CH_3$), 2.2-2.9 (16H, m, $CH_2$), 3.40 (4H, S, N—H) 4.93 (4H, S, N—$CH_2$) 6.8-7.4 (16H, m, Arom-H).

IR$\upsilon_{max}$nujol $cm^{-1}$: 3460, 3360(N—H); 1630(C=N).

EXAMPLE 4

Synthesis of Dimer (II-4)

7.25 g (0.02 mole) of 2,2',6,6'-tetraisopropylphenyl-carbodiimide, 1.36 g (0.01 mole) of p-xylylenediamine were added to 20 ml of toluene. The mixture was heated and refluxed for 6 hours. After the mixture was cooled by standing, the deposited crystal was collected by filtration to obtain grayish white crystalline matter, which was recrystallized from toluene to obtain 1.5 g of white powder.

Melting point: 276°-279° C.

H-NMR (solvent:$CDCl_3$) δ: 0.7-1.5 (48H, m, —$CH_3$), 2.8-3.5 (8H, m, CH), 3.50 (4H, S, NH) 5.00 (4H, S, N—$CH_2$) 6.95-7.45 (16H, m, Arom-H).

IR$\upsilon_{max}$nujol $cm^{-1}$: 3500, 3390(N—H); 1620(C=N).

EXAMPLE 5

Synthesis of Dimer (II-5)

7.6 g (0.02 mole) of N,N'-di(2,6-diisopropylphenyl)-guanidine, 2.6 g (0.01 mole) of α,α'-dibromo-m-xylene, and 1.1 g (0.01 mole) of anhydrous sodium carbonate were added to 50 ml of benzene. The mixture was heated and refluxed for 2 hours. Having been cooled by standing, the mixture was filtered to eliminate insoluble matter and the solvent was distilled off under reduced pressure to obtain pale brown powder, which was recrystallized from acetone to obtain 1.4 g of white powder.

Melting point: 240°-242° C.

H-NMR (solvent:$CDCl_3$) δ: 0.7-1.4 (48H, m, —$CH_3$), 2.8-3.5 (8H, m, —CH), 3.46 (4H, S, NH) 4.95 (4H, S, N—$CH_2$) 6.8-7.7 (16H, m, Arom-H).

IR$\upsilon_{max}$nujol $cm^{-1}$: 3490, 3380(N—H); 1630(C=N).

EXAMPLE 6

Synthesis of Dimer (II-6)

1.0 g of grayish white powder was obtained in the same manner as in Example 5 except that 2.6 g (0.01 mole) of α,α'-dibromo-o-xylene was used as the dihalogenoxylene.

Melting point: 175°-179° C.

H-NMR (solvent:$CDCl_3$) δ: 0.9-1.4 (48H, m, —$CH_3$), 2.8-3.6 (8H, m, —CH), 4.1 (4H, m, NH) 4.8 (4H, S, N—$CH_2$) 7.0-7.4 (16H, m, Arom-H).

IR$\upsilon_{max}$nujol $cm^{-1}$: 3376(N—H); 1630(C=N).

EXAMPLE 7

Synthesis of Dimer (II-7)

7.6 g (0.02 mole) of N,N'-di(2,6-diisopropylphenyl)-guanidine, and 0.6 g (0.01 mole) of acrolein were added to 100 ml of diglyme. The mixture was heated to 110° C. and stirred at this temperature for 5 hours. Having been cooled by standing, the mixture was poured into a large amount of water, and extracted with chloroform. The chloroform solution was washed with water, and concentrated to obtain pale brown crystalline matter, which was recrystallized from benzene to obtain 4.2 g of white powder.

Melting point: 217°-221° C.

H-NMR (solvent:$CDCl_3$) δ: 0.9-1.50 (48H, m, —$CH_3$), 2.9-3.6 (8H, m, —CH), 4.0 (2H, d, N—$CH_2$ 4.9(1H, d, m, =CH—), 5.3 (4H, m, NH), 6.0 (1H, d, N=CH) 6.9-7.4 (12H, m, Arom-H).

IR$\upsilon_{max}$nujol $cm^{-1}$: 3500, 3400(N—H); 1630(C=N); 1580(C=C); 1285(C—N).

EXAMPLE 8

Synthesis of Dimer (II-8)

1.8 g of pale yellow powder was obtained in the same manner as in Example 1, except that 11.4 g (0.03 mole) of N,N'-di(2-phenylphenyl)thiourea was used as thio urea instead of N,N'-di(2,5-dimethylphenyl)thiourea.

Melting point: 195°-199° C.

H-NMR (solvent:$CDCl_3$) δ: 3.3 (4H, S, NH) 5.05 (4H, S, N—$CH_2$) 6.6-7.4 (40H, m, Arom-H).

IR$\upsilon_{max}$nujol $cm^{-1}$: 3460, 3380(N—H; 1650(C=N).

EXAMPLE 9

Synthesis of Dimer (II-9)

1.7 g of pale brown powder was obtained in the same manner as in Example 5 except that 5.4 g (0.02 mole) of N,N'-di(4-methoxyphenyl)guanidine was used as the guanidine.

Melting point: 131°-134° C.

H-NMR (solvent:$CDCl_3$) δ: 3.55 (4H, S, NH), 3.75 (12H, d, $OCH_3$), 4.95 (4H, S, N—$CH_2$) 6.6-7.2 (20H, m, Arom-H).

IR$\nu_{max}$nujol $cm^{-1}$: 3470, 3340(N—H); 1640(C=N); 1250, 1230 (C—O).

EXAMPLE 10

Synthesis of Dimer (II-10)

2.5 g of grayish white powder was obtained in the same manner as in Example 1 except that 9.8 g (0.03 mole) of N,N'-di-1-naphthylthiourea as the thiourea and 2.0 g (0.015 mole) of m-xylylenediamine as the diamine was used.

Melting point: 169°-172° C.

H-NMR (solvent:$CDCl_3$) δ: 4.9 (4H, S, NH) 5.1 (4H, S, N—$CH_2$) 7.0-8.3 (32H, m, Arom-H).

IR$\nu_{max}$nujol $cm^{-1}$: 3460, 3390(N—H); 1660(C=N).

EXAMPLE 11

Synthesis of Compound (I-1)

7.6 g (0.02 mole) of bis(2,6-diisopropylphenyl)guanidine and 2.8 g (0.015 mole) of 1,2-dibromoethane were stirred in 100 ml of dimethylformamide, under nitrogen atmosphere at 100° C. for 2 hours. Thereafter, the solvent was distilled off under reduced pressure. The residual matter was extracted with chloroform, neutralized with an aqueous sodium carbonate solution, washed with water, and concentrated to obtain pale brown crystalline matter. This crystalline matter was recrystallized from chloroform to obtain 2.4 g of grayish white powder of the aforementioned dimer (I-1).

Melting point: 260°-267° C.

H-NMR (solvent:$CDCl_3$) δ: 1.20 (48H, d, $CH_3$), 3.21 (8H, m, CH), 5.60 (2H, S, N—$CH_2$) 7.0 (4H, broad S, NH), 7.15-7.40 (12H, m, Arom-H).

IR$\nu_{max}$nujol $cm^{-1}$: 3460(N—H); 1360(C=N).

EXAMPLE 12

| | |
|---|---|
| Styrene/butyl methacrylate (80/20) copolymer (weight-average molecular weight $M_w$: 350,000) | 100 parts |
| Magnetite | 60 parts |
| Low-molecular-weight polypropylene wax | 3 parts |
| Dimer (II-4) | 2 parts |

The above materials were blended sufficiently with a blender, and kneaded with a double-screw kneading extruder set at a temperature of 150° C. The resulting kneaded matter was cooled and granulated with a cutter mill. Then it is pulverized with a pulverizer employing a jet stream. The resulting fine powder was classified with a fixed-wall type air-separation classifier to obtain a classified powdery material.

The classified powdery material was treated with a multi-fraction classifier (Elbow Jet Classifier made by Nittetsu Kogyo K.K.) utilizing Coanda effect to eliminate ultra-fine powder and coarse powder exactly, giving black fine powder (a magnetic toner) having a volume-average particle diameter of 11.5 μm.

0.5 parts of hydrophobic dry silica having positive chargeability (BET specific surface area: 200 $m^2/g$) was added to 100 parts of the resulting black fine powder of a magnetic toner, and the mixture was blended by using Henschel mixer to provide a positive-chargeable one-component magnetic toner.

The resulting toner was subjected to a 50,000-sheet copying test by using a commercial electrophotographic copying machine NP-3525 (made by Canon K.K.) in the environment of a temperature of 23° C. and humidity of 60% RH. Sharp images were obtained from the beginning with an image density of 1.41. Even after 50,000 sheets of copying, the image was sharp with image density of 1.39 without fogging. The triboelectric charge of the toner on the developing sleeve was measured to be +6.3 μc/g at the beginning, and +5.5 μc/g after 50,000 sheets of copying. Contamination of the sleeve was hardly observed after 50,000 sheets of copying.

Similar image-forming tests were conducted at a temperature of 15° C. and a humidity of 10% RH, and at a temperature of 35° C. and a humidity of 85% RH. At the temperature of 15° C. and the humidity of 10% RH, satisfactory toner images were obtained with image densities of 1.42 at the beginning, and 1.38 after 50,000 sheets of copying. Even in an environment at the temperature of 35° C. and a humidity of 85% RH, satisfactory toner images were obtained with image densities of 1.37 at the beginning, and 1.35 after 50,000 sheets of copying.

EXAMPLE 13

| | |
|---|---|
| Copolymer of styrene/butyl acrylate/divinylbenzene (comonomer weight ratio 80/19.5/0.5, $M_w$: 350,000) | 100 parts |
| Magnetite | 80 parts |
| Low-molecular-weight polypropylene wax | 4 parts |
| Dimer (II-9) | 2 parts |

The above materials were blended sufficiently with a blender, and kneaded with a double-screw kneading extruder set at a temperature of 150° C. The resulting kneaded matter was cooled and granulated with a cutter mill. Then it is pulverized with a pulverizer employing a jet stream. The resulting powder was classified with a fixed-wall type air-separation classifier to obtain a classified powdery material.

The classified powdery material was treated with a multi-fraction classifier (Elbow Jet Classifier made by Nittetsu Kogyo K.K.) utilizing Coanda effect to eliminate ultra-fine powder and coarse powder exactly, giving a black fine powdery material (a magnetic toner) having volume-average particle diameter of 7.2 μm.

0.6 parts of hydrophobic dry silica having positive chargeability (BET specific surface area: 200 $m^2/g$) was added to 100 parts of the resulting black fine powder of a magnetic toner, and the mixture was blended by using Henschel mixer to provide a positive-chargeable one-component magnetic toner.

The resulting magnetic toner was subjected to copying tests by using a commercial electrophotographic copying machine NP-3525 (made by Canon K.K.).

Under the environment of a temperature of 23° C. and humidity of 60% RH, clear images were obtained from the beginning with an image density of 1.38. Even after 50,000 sheets of copying, the image was satisfactory with image density of 1.36. The triboelectric charge of the toner on the developing sleeve was measured to be +6.8 μc/g at the beginning, and +5.2 μc/g after 50,000 sheets of copying. No contamination of the sleeve was hardly observed even after 50,000 sheets of copying.

Under the environment of a temperature of 15° C. and a humidity of 10% RH, satisfactory toner images were obtained with image densities of 1.38 at the beginning, and 1.37 after 50,000 sheets of copying.

Even under the environment of the temperature of 35° C. and the humidity of 85% RH, satisfactory toner images were obtained with image densities of 1.36 at the beginning, and 1.36 after 50,000 sheets of copying.

COMPARATIVE EXAMPLE 1

A magnetic toner having a volume-average particle diameter of 7.3 μm was prepared in the same manner as in Example 13, except that 4 parts of the guanidine derivative shown below was used instead of the dimer (II-9) used in Example 13, and the resulting toner was subjected to copying tests.

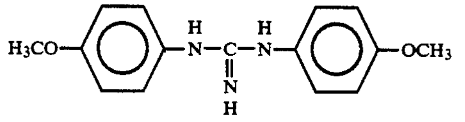

In the environment of a temperature of 23° C. and a humidity of 60% RH, sharp images were obtained from the beginning with an image density of 1.40. However, after 50,000 sheets of copying, the image density was 1.21, exhibiting tendency of falling slightly. The triboelectric charge of the magnetic toner on the developing sleeve was measured to be +6.1 μc/g at the beginning. After 50,000 sheets of copying, it fell to +2.7 μc/g, and contamination of the sleeve was observed. In the environments of a temperature of 15° C. and humidity of 10% RH, and a temperature of 35° C. and humidity of 85% RH, satisfactory images were obtained at the beginning with image densities of 1.41, and 1.37, respectively, thus no problems arising on environment dependency. However, after 50,000 sheets of copying, the image density decreased to 1.23, and 1.16, respectively, because of sleeve contamination.

For the purpose of preventing the sleeve contamination, a toner was prepared by reducing the amount of the above-described guanidine derivative (bis(p-methoxyphenyl)guanidine) to two parts. In image formation at a temperature of 23° C. and humidity of 60% RH, although no decrease of the image density caused by sleeve contamination occurred, the image density was as low as 1.21 from the beginning.

EXAMPLE 14

| | |
|---|---|
| Styrene/butyl methacrylate (80/20) copolymer (weight-average molecular weight $M_w$: 350,000) | 100 parts |
| Carbon black | 5 parts |
| Low-molecular-weight polypropylene wax | 2 parts |
| Dimer (II-1) | 2 parts |

The above materials were blended sufficiently with a blender, and kneaded with a double-screw kneading extruder set at a temperature of 150° C. The resulting kneaded matter was cooled and granulated with a cutter mill. Then it is pulverized with a pulverizer employing a jet stream. The resulting fine powder was classified with a fixed-wall type air-separation classifier to obtain a classified powdery material.

The classified powdery material was treated with a multi-fraction classifier (Elbow Jet Classifier made by Nittetsu Kogyo K.K.) utilizing Coanda effect to eliminate ultra-fine powder and coarse powder exactly, giving a black fine powder (a magnetic toner) having a volume-average particle diameter of 11.8 μm.

Five parts of this fine black powder was mixed with 100 parts of powdery iron carrier of 50–80 μm in average particle diameter to prepare a developing agent. Separately a negative electrostatic image was formed on an OPC photosensitive member according to a known electrophotography. This image was developed to give a toner image by using the above developing agent according to a magnetic brush method, and the toner image was transferred on a sheet of plain paper, and was heated and fixed thereon.

The resulting image was sharp, having a sufficient image density of as high as 1.42. The image density after 20,000 sheets of copying was 1.39, no deteriation of the image quality being observed. Triboelectrical charge of the toner was measured to be +13.8 μc/g at the beginning, and +13.3 μc/g after 10,000 sheets of copying according to a blow-off method, thus the decrease of the charge being little.

COMPARATIVE EXAMPLE 2

A toner was prepared and subjected to a copying test in the same manner as in Example 14 except that 5 parts of benzylmethylhexadecylammonium chloride was used instead of 2 parts of the dimer (II-1) used in Example 14.

As the results, the image density was as low as 1.05 at the beginning, which did not increase during repeated copying.

EXAMPLE 15

| | |
|---|---|
| Styrene/butyl methacrylate (80/20) copolymer (weight-average molecular weight $M_w$: 350,000) | 100 parts |
| Copper phthalocyanine blue pigment | 5 parts |
| Low-molecular-weight polypropylene wax | 2 parts |
| Dimer (I-1) | 1 parts |

The above materials were blended sufficiently with a blender, and kneaded with a double-screw kneading extruder set at a temperature of 150° C. The resulting kneaded matter was cooled and granulated with a cutter mill. Then it is pulverized with a pulverizer employing a jet stream. The resulting fine powder was classified with a fixed-wall type air-separation classifier to obtain a classified powdery material.

The classified powdery material was treated with a multi-fraction classifier (Elbow Jet Classifier made by Nittetsu Kogyo K.K.) utilizing Coanda effect to eliminate ultra-fine powder and coarse powder exactly, giving a fine powder (a cyan toner) having a volume-average particle diameter of 11.6 μm.

To 100 parts of the resulting fine powder, 0.4 parts of hydrophobic dry silica having positive chargeability (BET specific surface area: 200 $m^2/g$) was added, and the mixture was blended with a Henschel mixer to prepare a positively chargeable cyan toner.

8 parts of the resulting cyan toner was added to 100 parts of a fluororesin-acrylic resin-coated ferrite carrier having an average particle diameter of 65 μm to give a two-component developing agent.

This two-component developing agent was subjected to a copying test with a commercial copying machine (NP-5540 (trade name), made by Canon K.K.).

In an environment of a temperature of 23° C., and a humidity of 60% RH, sharp blue toner images were obtained with an image density of 1.35 in the beginning of the test. Even after 10,000 sheets of copying a clear blue image was obtained with an image density of 1.33 without declining of the image quality.

The copying tests were also conducted in environments of a temperature of 35° C. and a humidity of 85% RH, and of a temperature of 15° C. and a humidity of 10% RH. The results were as satisfactory as in the test at the temperature of 23° C. and the humidity of 60% RH.

EXAMPLE 16

| | |
|---|---|
| Styrene/butyl acrylate copolymer (copolymerization weight ratio = 80:20, $M_w$: 300,000) | 100 parts |
| Copper phthalocyanine blue pigment (C.I. Pigment Blue 15) | 5 parts |
| Dimer (II-4) | 2 parts |

The above materials were blended sufficiently with a blender, and kneaded with a double-screw kneading extruder set at a temperature of 150° C. The resulting kneaded matter was cooled and granulated with a cutter mill. Then it was pulverized with a pulverizer employing a jet stream. The resulting fine powder was classified with a fixed-wall type air-separation classifier to obtain a classified powdery material.

The classified powdery material was treated with a multi-fraction classifier (Elbow Jet Classifier made by Nittetsu Kogyo K.K.) utilizing Coanda effect to eliminate ultra-fine powder and coarse powder exactly, giving a fine powdery material (a cyan toner) having a volume-average particle diameter of 12.2 μm.

To 100 parts of the resulting fine powdery material, 0.4 parts of hydrophobic dry silica having positive chargeability (BET specific surface area: 200 $m^2/g$) was added, and the mixture was blended with a Henschel mixer to prepare a positively chargeable cyan toner.

4 parts of the resulting cyan toner was added to 100 parts of a fluororesin-acrylic resin-coated ferrite carrier having an average particle diameter of 65 μm to prepare a two-component developing agent.

This developing agent was employed in copying tests by use of a modified commercial color electrophotographic copying machine CLC-1 (made by Canon K.K.) which had been modified by replacing the OPC photosensitive drum by an amorpous silicon drum.

As the results, under environmental conditions of a temperature of 23° C., and a humidity of 60% RH, sharp blue toner images were obtained with an image density of 1.32 at the beginning of the test. Even after 20,000 sheets of copying, the image quality did not become lowered.

The copying tests were also conducted under environmental conditions of a temperature of 35° C. and a humidity of 85% RH, and of a temperature of 15° C. and a humidity of 10% RH. The results were as satisfactory as in the test at the temperature of 23° C. and the humidity of 60% RH.

EXAMPLE 17

A fine powdery material (a magenta toner) having a volume-average particle diameter of 11.8 μm was prepared in the same manner as in Example 16 except that the 5 parts of the copper phthalocyanine pigment (C.I. Pigment Blue 15) in Example 16 was replaced by 1.0 part of a quinacridone pigment (C.I. Pigment Red 122). This fine powdery material was mixed with hydrophobic dry silica having positive chargeability to obtain a positively chargeable magenta toner.

Further the toner was mixed with the same carrier in the same ratio as in Example 16 to prepare a two-component developing agent.

This two-component developing agent was subjected to a copying test in the same manner as in EXAMPLE 16

As the results, under environmental conditions of a temperature of 23° C., and a humidity of 60% RH, sharp magenta toner images were obtained with an image density of 1.35 at the beginning of the test. Even after 20,000 sheets of copying, the image quality did not become lowered.

The copying tests were also conducted under environmental conditions of a temperature of 35° C. and a humidity of 85% RH, and of a temperature of 15° C. and a humidity of 10% RH. The results were as satisfactory as in the test at the temperature of 23° C. and the humidity of 60% RH.

EXAMPLE 18

A fine powdery material (a yellow toner) having a volume-average particle diameter of 12.0 μm was prepared in the same manner as in Example 16 except that the 5 parts of the copper phthalocyanine pigment (C.I. Pigment Blue 15) in Example 16 was replaced by 3.5 parts of C.I. Pigment Yellow 17. This powdery material was mixed with hydrophobic dry silica having positive chargeability to obtain a positively chargeable yellow toner.

Further the toner was mixed with the same carrier in the same ratio as in Example 16 to prepare a two-component developing agent.

This two-component developing agent was subjected to a copying test in the same manner as in Example 16.

As the results, under environmental conditions of a temperature of 23° C., and a humidity of 60% RH, sharp yellow toner images were obtained with an image density of 1.28 at the beginning of the test. Even after 20,000 sheets of copying, the image quality did not become lowered.

The copying tests were also conducted under environmental conditions of a temperature of 35° C. and a humidity of 85% RH, and of a temperature of 15° C. and a humidity of 10% RH. The results were as satisfactory as in the test at the temperature of 23° C. and the humidity of 60% RH.

EXAMPLE 19

A fine powdery material (a black toner) having a volume-average particle diameter of 12.3 μm was prepared in the same manner as in Example 16 except that the 5 parts of the copper phthalocyanine pigment (C.I. Pigment Blue 15) in Example 16 was replaced by 3 parts of carbon black. This fine powdery material was mixed with hydrophobic dry silica having positive chargeability to obtain a positively chargeable black toner.

Further the toner was mixed with the same carrier in the same ratio as in Example 16 to prepare a two-component developing agent.

This two-component developing agent was subjected to a copying test in the same manner as in Example 16.

As the results, under environmental conditions of a temperature of 23° C., and a humidity of 60% RH, sharp black toner images were obtained with an image density of 1.37 at the beginning of the test. Even after 20,000 sheets of copying, the image quality did not become lowered.

The copying tests were also conducted under environmental conditions of a temperature of 35° C. and a humidity of 85% RH, and of a temperature of 15° C. and a humidity of 10% RH. The results were as satisfactory as in the test at the temperature of 23° C. and the humidity of 60% RH.

EXAMPLE 20

By employing the cyan, magenta, yellow, and black developing agents used in Examples 16 to 19, satisfactory full color toner images were obtained.

EXAMPLE 21

Copolymer of styrene/butyl acrylate/butyl maleate half ester/divinyl benzene (copolymerization weight

| | |
|---|---|
| ratio = 80:15.5:3.9:0.6, acid value:20, $M_w$: 300,000 | 100 Parts |
| Magnetite | 80 parts |
| Low-molecular-weight polypropylene wax | 4 parts |
| Dimer (II-8) | 4 parts |

With the materials above, a black fine powdery material (a magnetic toner) having a volume-average particle diameter of approximately 8 μm was prepared in the same manner as in Example 13.

0.5 parts of hydrophobic dry silica having positive chargeability (BET specific surface area: 200 $m^2/g$) was added to 100 parts of the resulting black fine powdery material, and the mixture was blended by Henschel mixer to provide a positive-chargeable one-component magnetic toner.

The magnetic toner was subjected to a 50,000-sheet copying test in an environment of a temperature of 23° C. and humidity of 60% RH by means of a commercial electrophotographic copying machine NP-3525 (made by Canon K.K.). Sharp images were obtained with an image density of 1.35 from the beginning. Even after 50,000 sheets of copying, the image was sharp with image density of 1.34 without fogging. The triboelectric charge of the magnetic toner on the sleeve was measured to be 7.1 μc/g.

5 parts by weight of the magnetic toner was mixed with 95 parts by weight of iron powder carrier. The magnetic toner had a triboelectrical charge of +11.3 μc/g as measured according to a blow-off method.

COMPARATIVE EXAMPLE 3

A fine black powdery material (a magnetic toner) having a volume-average particle diameter of approximately 8 μm was prepared in the same manner as in Example 21 except that 2 parts of the guanidine derivative below was used instead of Dimer (II-8).

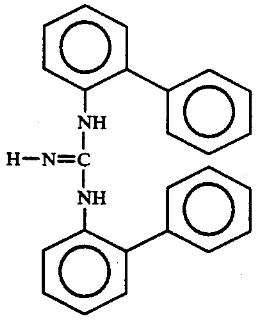

0.5 parts of hydrophobic dry silica having positive chargeability (BET specific surface area: 200 $m^2/g$) was added to 100 parts of the resulting black fine powdery material, and the mixture was blended by using a Henschel mixer to provide a positively-chargeable one-component magnetic toner.

The magnetic toner was subjected to a 50,000-sheet copying test in an environment of a temperature of 23° C. and humidity of 60% RH by means of a commercial electrophotographic copying machine NP-3525 (made by Canon K.K.). Sharp images were obtained with an image density of 1.20 at the beginning. After 50,000 sheets of copying, the image density was 1.15.

The triboelectric charge of the magnetic toner on the sleeve was measured to be +4.8 μc/g.

5 parts by weight of the magnetic toner was mixed with 95 parts by weight of iron powder carrier. The magnetic toner had a triboelectric charge of +8.5 μc/g as measured according to a blow-off method.

The guanidine derivative used in this Comparative Example 3 is considered to react partially with the resin having an acid value.

EXAMPLE 22

| | |
|---|---|
| Copolymer of styrene/butyl acrylate/butyl maleate half ester/divinyl benzene (copolymerization weight ratio = 80:15.5:3.9:0.6, acid value:20, $M_w$: 300,000) | 100 parts |
| Copper phthalocyanine blue pigment | 5 parts |
| Low-molecular-weight polypropylene wax | 3 parts |
| Dimer (II-8) | 3 parts |

With the materials above, a fine powdery material (a cyan toner) having a volume-average particle diameter of approximately 12 μm was prepared in the same manner as in Example 15.

0.4 parts of hydrophobic dry silica having positive chargeability (BET specific surface area: 200 $m^2/g$) was added to 100 parts of the resulting fine powdery material, and the mixture was blended by Henschel mixer to provide a positive-chargeable cyan toner.

8 parts of the resulting cyan toner was added to 100 parts of a fluororesin-acrylic resin-coated ferrite carrier having an average particle diameter of 65 μm to give a two-component developing agent.

This two-component developing agent was subjected to a copying test by using a commercial copying machine (NP-5540 (trade name), made by Canon K.K.).

In an environment of a temperature of 23° C., and a humidity of 60% RH, sharp blue toner images were obtained with an image density of 1.37 in the beginning of the test. Even after 10,000 sheets of copying, sharp blue image were obtained with an images density of 1.35 without deterioration of the image quality.

The triboelectric charge of the cyan toner in the mixture of 8 parts of the resulting cyan toner and 100 parts of the fluorine-acryl-coated ferrite carrier was measured to be +36 μc/g according to a blow-off method.

COMPARATIVE EXAMPLE 4

A fine powdery material (a cyan toner) having a volume-average particle diameter of approximately 12 μm was prepared in the same manner as in Example 22 except that 3 parts of the guanidine derivative below was used instead of Dimer (II-8).

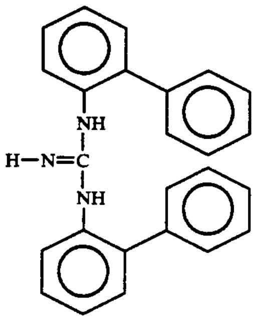

0.4 parts of hydrophobic dry silica having positive chargeability (BET specific surface area: 200 $m^2/g$) was added to 100 parts of the resulting fine powdery material, and the mixture was blended by using a Henschel mixer to provide a positively-chargeable cyan toner.

8 parts of the resulting cyan toner was added to 100 parts of a fluororesin-acrylic resin-coated ferrite carrier having an average particle diameter of 65 μm to provide a two-component developing agent.

This two-component developing agent was subjected to a copying test with a commercial copying machine (NP-5540 (trade name), made by Canon K.K.).

In an environment of a temperature of 23° C., and a humidity of 60% RH, blue toner images were obtained with an image density of 1.20 in the beginning of the test. After 10,000 sheets of copying, the blue toner images were obtained with an image density of 1.18.

The triboelectric charge of the cyan toner in the mixture of 8 parts of the resulting cyan toner and 100 parts of the fluorine-acryl-coated ferrite carrier was measured to be +21 μc/g according to a blow-off method. The value of the triboelectric charge was lower than that of the toner in Example 22. This is considered to be caused by a partial reaction of the guanidine derivative used in Comparative Example 4 with the resin having an acid value.

What is claimed is:

1. A dimer of a diarylguanidine type compound represented by the formula (II):

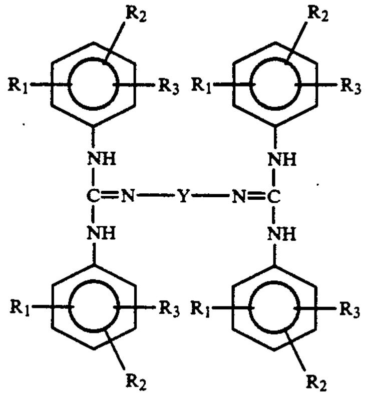

(II)

wherein $R^1$, $R^2$, and $R^3$ are respectively hydrogen, an alkyl group of 1 to 4 carbons, an alkoxy group of 1 to 5 carbons, or a phenyl group, which may be the same or different from each other, and adjacent groups may be linked together to form a fused phenyl ring, and Y is

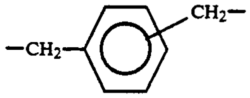

or $-CH{=}CH-CH_2-$.

2. A dimer according to claim 1, having the following formulas:

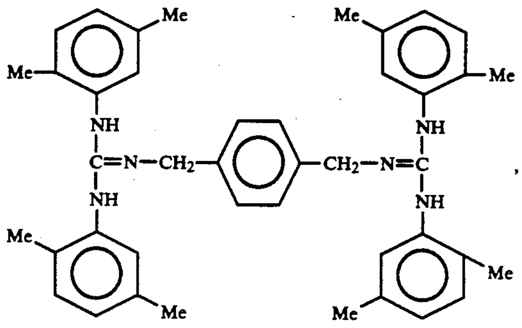

,

-continued
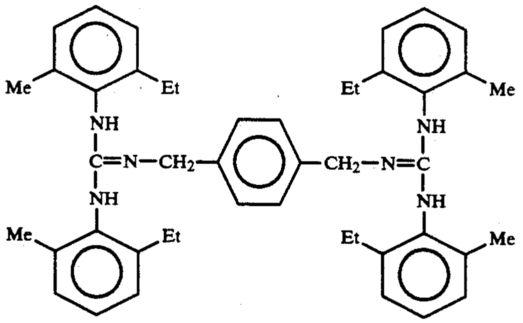
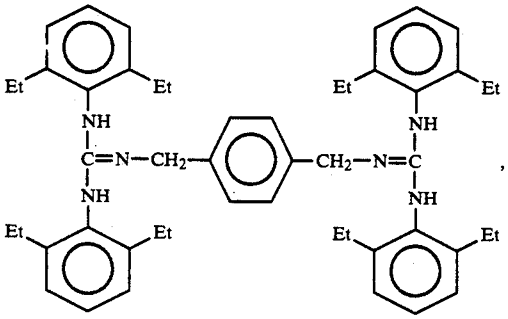
,
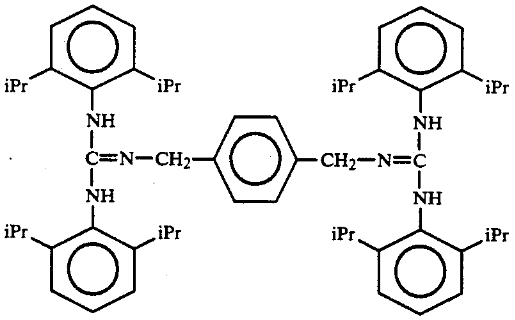
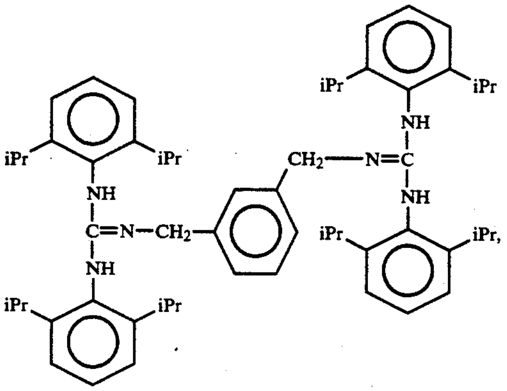
,

-continued
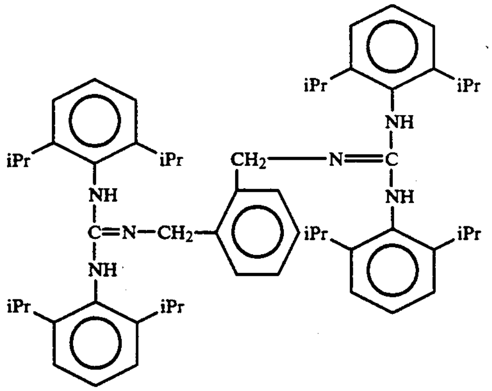
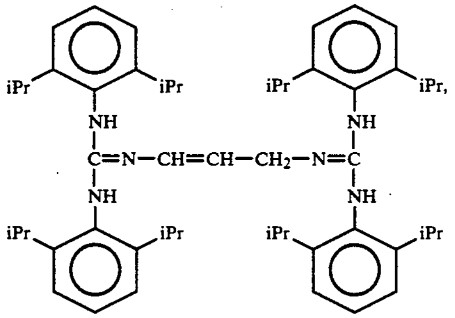
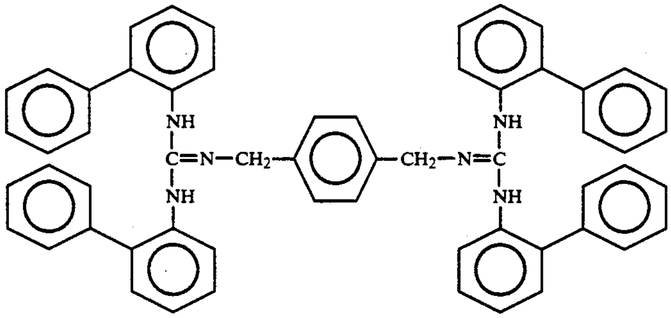
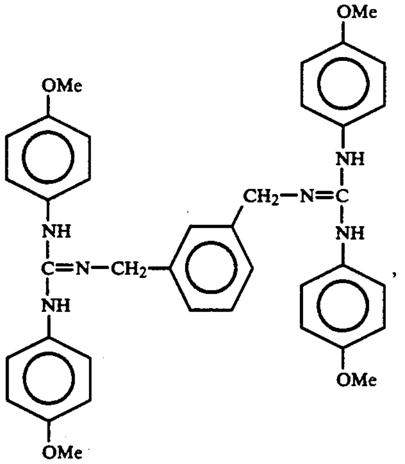

-continued
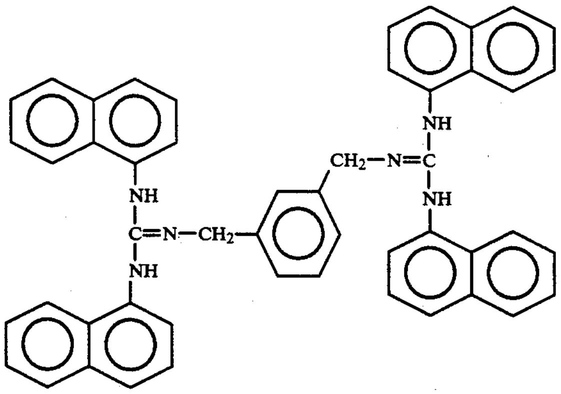
wherein Me denotes a methyl group, Et an ethyl group, and iPr an isopropyl group.
* * * * *

UNITED STATES PATENT AND TRADEMARK OFFICE

CERTIFICATE OF CORRECTION

PATENT NO. : 5,214,208

DATED : May 25, 1993

INVENTOR(S) : KATSUHIKO TANAKA, ET AL.

It is certified that error appears in the above-identified patent and that said Letters Patent is hereby corrected as shown below:

COLUMN 1

Line 30, "used," should be deleted.
Line 31, "used" should read --used,--.
Line 37, "are" should read --is--.

COLUMN 2

Line 7, "a" should be deleted.
Line 15, "a" should be deleted.

COLUMN 3

Line 1, "with" should be deleted.
Line 3, "ring," should read --fused ring,--.
Line 42, "with" should be deleted.
Line 44, "ring," should read --fused ring,--.
Line 57, close up left margin.

COLUMN 4

Line 1, "a" should be deleted.

COLUMN 5

Line 21, "including" should read --include--.
Line 24, "including" should read --include--.
Line 26, "R1" should read --$R^1$--.
Line 27, "R6" should read --$R^6$--.
In Dimer (I-1), "$C{=}CH_2{-}N{=}C$" should read --$C{=}N{-}CH_2{-}N{=}C$--.

UNITED STATES PATENT AND TRADEMARK OFFICE
CERTIFICATE OF CORRECTION

PATENT NO. : 5,214,208

DATED : May 25, 1993

INVENTOR(S) : KATSUHIKO TANAKA, ET AL.

It is certified that error appears in the above-identified patent and that said Letters Patent is hereby corrected as shown below:

COLUMN 6

Line 52, "a" should be deleted.

COLUMN 7

Line 2, "include" should read --includes--.

COLUMN 9

Line 41, "and" should read --or--.

COLUMN 10

Line 21, "66," should read --66--.

COLUMN 13

Line 31, "H—H)" should read --N—H)--.
Line 39, "dine" should read --dine,--.

COLUMN 14

Line 47, "N—$CH_2$" should read --N—$CH_2$),--.
Line 62, "(N—H;" should read --(N—H);--.

COLUMN 17

Line 1, "hardly" should be deleted.

UNITED STATES PATENT AND TRADEMARK OFFICE

CERTIFICATE OF CORRECTION

PATENT NO. : 5,214,208
DATED : May 25, 1993
INVENTOR(S) : KATSUHIKO TANAKA, ET AL.

It is certified that error appears in the above-identified patent and that said Letters Patent is hereby corrected as shown below:

COLUMN 17

Line 40, "arising" should read --arose--.
Line 65, "is" should read --was--.

COLUMN 19

Line 7, "copying" should read --copying,--.

COLUMN 20

Line 11, "EXAMPLE" should read --Example--.
Line 12, "16" should read --16.--.
Line 64, "Further" should read --Further,--.

COLUMN 21

Lines 23-24 should be deleted.
Line 27, insert: --Copolymer of styrene/butyl acrylate/butyl maleate half ester/divinyl benezene (copolymerization weight--.

UNITED STATES PATENT AND TRADEMARK OFFICE
CERTIFICATE OF CORRECTION

PATENT NO. : 5,214,208

DATED : May 25, 1993

INVENTOR(S) : KATSUHIKO TANAKA, ET AL.

It is certified that error appears in the above-identified patent and that said Letters Patent is hereby corrected as shown below:

COLUMN 23

Line 1, "image" should read --images-- and "images" should read --image--.

Signed and Sealed this

Fifteenth Day of March, 1994

Attest:

BRUCE LEHMAN

Attesting Officer

*Commissioner of Patents and Trademarks*